US007754488B2

(12) United States Patent
Richardson et al.

(10) Patent No.: US 7,754,488 B2
(45) Date of Patent: Jul. 13, 2010

(54) RAPID ANALYSIS OF FUNCTIONAL FLUIDS

(75) Inventors: Robert C. Richardson, Tomball, TX (US); Richard J. Vickerman, Stow, OH (US); Mark R. Baker, Lyndhurst, OH (US); Gregory D. Taylor, Madison, OH (US); Gary A. Garvin, Mentor, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 1183 days.

(21) Appl. No.: 10/823,219

(22) Filed: Apr. 13, 2004

(65) Prior Publication Data
US 2005/0227369 A1 Oct. 13, 2005

(51) Int. Cl.
G01N 33/22 (2006.01)
G01N 33/26 (2006.01)

(52) U.S. Cl. .............................. 436/60; 436/61; 422/56; 422/61

(58) Field of Classification Search ................... 436/60, 436/61; 422/56, 61
See application file for complete search history.

(56) References Cited

U.S. PATENT DOCUMENTS

| | | | | |
|---|---|---|---|---|
| 2,770,530 | A | 11/1956 | Bergstrom et al. | 23/230 |
| 3,238,020 | A | 3/1966 | Eiseman et al. | 23/253 |
| 3,580,704 | A | 5/1971 | Pickup et al. | 23/230 |
| 3,719,267 | A | 3/1973 | Reist et al. | 198/76 |
| 4,203,725 | A | 5/1980 | Snowden, Jr. et al. | 23/230 HC |
| 4,451,860 | A | 5/1984 | Honjo et al. | 360/77 |
| 4,654,309 | A | * 3/1987 | Mlinar et al. | 436/61 |
| 4,793,977 | A | 12/1988 | Morris | 422/55 |
| 5,313,824 | A | 5/1994 | Herguth et al. | 73/53.05 |

(Continued)

FOREIGN PATENT DOCUMENTS

| | | |
|---|---|---|
| EP | 0887644 A1 | 12/1998 |
| JP | 2539768 B2 | 2/1989 |
| WO | WO 03/078551 | 9/2003 |

OTHER PUBLICATIONS

Corresponding International Application No. PCT/US2005/012936 Search Report mailed Nov. 7, 2005.

(Continued)

*Primary Examiner*—Lyle A Alexander
(74) *Attorney, Agent, or Firm*—Christopher D. Hilker; David M. Shold

(57) ABSTRACT

The invention relates to a method to analyze the condition of a functional fluid comprising:
(1) obtaining a sample of the used fluid;
(2) placing the sample of the fluid to a test medium;
(3) reacting the fluid with an indicator in the test medium;
(4) analyzing visually the results of the reactor resulting in the determination of the condition of the fluid.

Further an apparatus for analyzing functional fluids is disclosed in the form of a test medium consisting of an absorbent or nonabsorbent material which has been treated with a chemical indicator, marker substance or a developer or detector reagent upon which a sample of the fluid to be tested is placed. The components in the treated test medium react with components in the test fluid providing a visual indication, for example a color change, to judge the condition, the presence of a marker substance or another parameter of the fluid. The functional fluid may be a lubricant, fuel or other functional fluid of innumerable sources, including internal combustion engines, turbines, transmissions, differentials, pumps, metalworking operations, cooling systems, etc, and be either organic solvent or aqueous based.

13 Claims, 1 Drawing Sheet

U.S. PATENT DOCUMENTS 5,710,372 A    1/1998   Becket .................. 73/53.01
6,598,464 B1   7/2003   Rossi ................... 73/53.01

OTHER PUBLICATIONS

Publication No. 58062559A2, Japanese Patent Office & Japio Abstract (Apr. 14, 1983, Masao et al.).

Publication No. 63063968A2, Japanese Patent Office & Japio Abstract (Mar. 22, 1988, Junichi et al.).

Publication No. 1046649A2, Japanese Patent Office & Japio Abstract (Feb. 21, 1989, Katsumi).

Publication No. 2035357A2, Japanese Patent Office & Japio Abstract (Feb. 5, 1990, Takayoshi).

Publication No. 4309862A2, Japanese Patent Office & Japio Abstract (Nov. 2, 1992, Takashi).

* cited by examiner

RAPID ANALYSIS OF FUNCTIONAL FLUIDS

FIELD OF THE INVENTION

The present invention relates to the analysis of functional fluids, including a method and apparatus for the analysis of functional fluids. In particular the functional fluids that are analyzed include lubricating fluids and fuels, such as those used in automobiles, trucks, engines, turbines, pumps, transmissions, differentials and the like.

BACKGROUND OF THE INVENTION

Methods exist for the analysis of functional fluids, including lubricating oils. In particular, methods and apparatus for testing the condition or identity of a fluid include chromatography and chemical analysis. These methods generally require controlled conditions and specialized training.

Other methods and apparatus for assessing the quality of a used fluid include placing a measured amount of fluid upon an absorbent material, heating the sample and awaiting dispersion of the sample. The amount of undispersed sample may then be measured and rated quantitatively. These methods and apparatus require significant controlled conditions, including measurement of the fluid sample volume, the use of a template to measure and rate the quantity of undispersed the sample. Additionally these methods can include heating of the sample, and awaiting dispersal of the sample. Another method to analyze oil is disclosed in U.S. Pat. No. 5,313,824; to Hergruth, et al. comprising the steps of obtaining a sample of the oil, placing the sample upon the medium, maintaining the medium in a desired position for an effective period of time for the spot to be visible, visually comparing the spotted test medium against comparative visual indicia depicting lubricating oil in various conditions, and selecting the comparative example which most closely resembles the test medium spotted with the test sample. No chemical reaction to occurs between the medium and the fluid, and it is just a visual observation of what the oil looks like compared to a standard.

Markers have been used to identify fluids. Proton accepting chemical substances, that at a solution concentration of below about 50 milligrams per liter, impart little or no significant color to organic solvents, have been proposed as markers, or taggants, especially for petroleum-derived fuels. The marker is dissolved in a liquid to be identified, and then subsequently detected by performing a chemical test on the marked liquid. Markers are sometimes employed by government agencies to ensure that the appropriate tax has been paid on particular grades of fuel. Oil companies also mark their products to help assist in identifying diluted or altered products. These companies often go to great expense to make sure their branded petroleum products meet certain specifications, for example, volatility and octane number, as well as to provide their petroleum products with effective additive packages containing detergents and other components. Consumers rely upon product names and quality designations to assure that the product being purchased is the quality desired. Thus, it is important to be able to identify a marker in a petroleum product.

Traditionally, the presence of a marker substance is detected and optionally quantified by extracting the fuel with an immiscible aqueous or significantly aqueous solution of an acid substance, the precise nature of which can be varied according to the characteristics of the marker substance. The acid reacts with the basic compound to produce a readily visible, more or less intensely colored cation, that is dissolved in the aqueous acid phase. This method is disclosed in U.S. Pat. No. 5,145,573. Additionally, a method has been disclosed in WO 03/078551 A2 where the acidic substance has been applied to a test strip. The test strip is dipped into the oil and diazo-type marker reacts with the acidic substance in the test strip and changes color.

The quantity of marker substance in the extract may also be measured, for instance, by visible light absorption spectrophotometry, the results of which are then compared with a reference standard to determine the original concentration of basic marker in the fluid. It may be necessary to make repeated, typically two or three, extractions of the fluid to recover the entire amount of marker originally present in order for complete quantification. Additionally, the extracted, separated phase is classifiable as a hazardous waste and presents problems of safe and lawful disposal, especially when examinations are made "in the field." Furthermore, the fluid with which was tested may be contaminated, making return to its original source undesirable and presenting additional waste disposal problems.

A need exists for a simple and rapid method of chemically analyzing a sample of a fluid on a qualitative basis to determine condition, origin or other useful property. The present invention will rapidly indicate the condition of a functional fluid such as lubricating oils, engine oil, transmission fluids, gear oils, hydraulic fluids, metalworking fluids, antifreeze fluids, coating system fluids, cooling systems fluids, farm tractor fluids, transformer fluids, fuels such as diesel, gasoline, biofuels, emulsified fuels, and the like in the field. Many owners/operators of equipment that depend on these functional fluids currently depend on standard guidelines, such as hours or mileage, to determine the appropriate interval to change the functional fluid (end of useful life). Additionally, labs are relied on today to determine the specific identify of a fluid, where a tool that would allow identification in the field would speed warranty resolution. Finally, since various absorbent materials (wipes, shop towels, paper towels, and napkins) are normally used in checking these functional fluids, it is conceived that the present invention combines the necessary utility of these absorbent materials with a diagnostic functionality that provides additional benefit.

SUMMARY OF THE INVENTION

It is the object of the present invention to provide a method to test the quality or the identity of a functional fluid in the field rapidly by untrained personnel and without precision measurement. It is a further object of the invention to provide a method to analyze functional fluids rapidly in the field. It is still a further object of the invention to provide a test kit for analysis of functional fluids rapidly in the field. Finally, since various absorbent materials (wipes, shop towels, paper towels, and napkins) are normally used in checking these functional fluids, it is conceived that the present invention combines the necessary utility of these absorbent materials with a diagnostic functionality that provides additional benefit.

These and other objectives are accomplished by providing a method and device to test functional fluids comprising a test medium treated with a chemical indicator or developing agent upon which the fluid is placed with accompanying descriptive text, and instructions.

The present invention provides a method to analyze the condition of a functional fluid comprising:
(1) obtaining a sample of the fluid;
(2) placing the sample of the fluid on a test medium;
(3) reacting the fluid with an indicator on or developing agent on the test medium; and
(4) analyzing the results of the reaction resulting in the determination of the condition of the fluid.

At a minimum, the visual indicia shows a depiction of a fluid which is in an acceptable condition and one where the fluid is in an unacceptable condition or a depiction of a marked and unmarked fluid. A greater range of conditions shown by the visual indicia will permit the test sample to be more closely approximated to the comparison examples by the kit user.

The invention further provides a test kit for the analysis of functional fluids comprising a chemically treated test medium and visual indicia depicting the functional fluids disposed upon the test medium. The invention further provides printed instructions, also included, to summarize the steps for use of the kit, which generally correspond to the description of the method given below.

The present invention further provides a novel and improved method for detecting marker substances. The method for the analysis of the quality of the functional fluid for example lubricating oil is effective but simple, and has the advantage of quickness and ease of use in uncontrolled conditions by untrained personnel. The invention provides a method to analyze function fluids which include lubricating oils, engine oils, transmission fluids, greases, gear oils, hydraulic fluids, metalworking fluids, antifreeze fluids, cooling system fluids, coating system fluid, farm tractor fluids, transformer fluids, fuels such as diesel, gasoline, biofuels, emulsified fuels, and the like.

BRIEF DESCRIPTION OF THE DRAWINGS

The foregoing aspects and many of the attendant advantages of the invention will become more readily appreciated as the same becomes better understood by reference to the following detailed description, when taken in conjunction with the accompanying figures.

DETAILED DESCRIPTION OF THE INVENTION

The present invention provides a method and device such as a kit for analyzing the condition of functional fluids. The functional fluids comes from innumerable sources, including internal combustion engines, turbines, transmissions, differentials, pumps, metalworking operations, cooling systems, and the like. The functional fluid includes organic solvent based, aqueous based and combinations thereof. The functional fluid includes lubricating oil, engine oil, gear oil, transmission fluids, hydraulic fluids, metalworking fluids, antifreeze fluids, cooling system fluids, coating system fluids, farm tractor fluids, transformer fluids, greases, fuels such as diesel, gasoline, biofuels, emulsified fuels, and the like.

Figure 1:
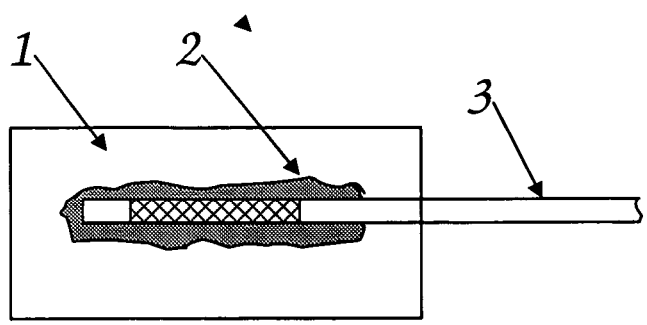
FIG. 1 is a drawing plain view showing application of the test sample to the test medium using a dipstick from an engine.

FIG. 1 is a plain view showing application of the test sample, 2, to the test medium, 1, using a dip stick, 3, from an engine.

Figure 2:
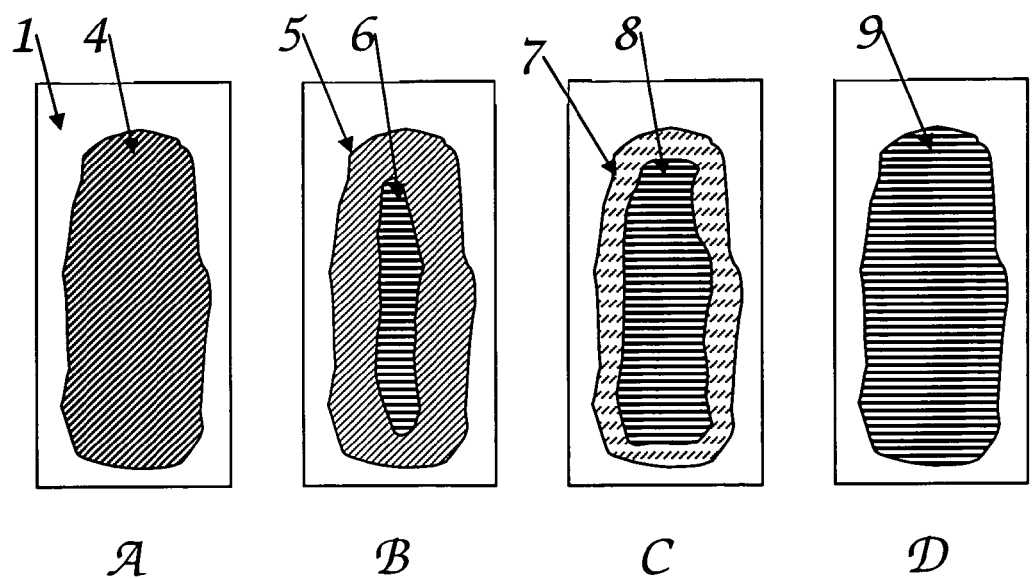
FIG. 2 is a drawing plain view showing dispersion of the lubricating oil sample upon the test medium for four fluids.

FIG. 2 is a plain view showing dispersion of the lubricating oil sample 2 upon the test medium 1 for four fluids: an engine oil in new condition, A; an engine oil in good condition, B; an engine oil that is acceptable within the normal range for typical engine oil, C; and an engine oil at the limit of useful life requiring an oil change, D. The different shading in the various drawings represents a progression in the degree of indicator color from the various samples of oil. Application of a new oil on the treated test medium, A, results in a dramatic color change of the indicator, 4. Application of an oil in good condition, B, results in a slightly less dramatic color change, 5, with a small amount of sludge in the center of the spot, 6. The oil in acceptable condition, C, gives a faint, but distinguishable color change, 7, with a larger sludge spot, 8. Finally, the spot formed from an oil in unacceptable condition, D, will have no apparent color change of the indicator, 9.

Test Medium

The functional fluid to be tested is placed upon an appropriate test medium. This test medium can be comprised of absorbent material, nonabsorbent material and combination thereof. The test medium includes paper, cellulosic material such as cellulose, cellulose nitrate, cellulose acetate, wood, chromatography paper, filter paper, polymeric fibers, natural fibers, finely woven fabrics, metal, glass, glass micro fiber, sintered glass, silica and/or alumina coated surfaces such as thin layer chromatography plates, plastic, plastic laminated material, composites and combinations thereof. The test medium must be capable of receiving a sample of the functional fluid. The test medium should be compatible with the indicator and/or developing agent. Other absorptive/adsorptive materials, having the, general physical properties and characteristics of chromatography paper are also be acceptable.

In one embodiment the preferred test medium includes "Whatman" white colored chromatography paper or filter paper in the form of an easy to dispense and use wipe. In one embodiment, absorptive paper, such as chromatography paper is preferred, in particular for lubricating oil samples. Light colored chromatography paper provides a consistent background which contrasts well with the functional fluid, provides for a more conspicuous color change and has the proper adsorptive affinity for the various components of an oil. For example, the coloration of the indicator becomes more pronounced over time on the outer edges of the sample spot on the paper as the indicator colored portion of the mixture is swept along with the mobile phase (oil and solvent) faster than the darker components of the used oil, such as sludge. This is due to the differences in adsorptive affinity for the paper. This difference in affinity becomes important as the concentration of sludge in the oil sample increases over the service life.

It is to be understood that depending on the type of fluid being analyzed and the particular functional purpose of the fluid, for instance, whether for gasoline powered engines as opposed to diesel powered engines, the test medium may need to be varied, whether the test medium is chromatography paper or other type of paper, polymeric fiber material or nonabsorbent material like glass, plastic or metal. The test medium may differ in its adsorptive affinity for the various components in the particular fluid, porosity, density, wicking ability, or other physical characteristics such as color.

The shape of the test medium is unimportant, so long as it is of an effective size to permit dispersion of the functional fluid sample, but small enough to be economical and limit waste. The test medium may be provided in a hermetically sealed envelope or package made of plastic or some other suitable material. The package could be designed to be held in the hand and opened on one side exposing the treated test medium for convenient usage yet protecting the users hand from contacting the test fluid or the indicator system adding to the convenience of the unit. Additionally, the test medium could be provided in a multi-unit dispenser tub for high volume applications in for example an automotive service station.

Indicator Reagents/Developing Agents

Indicator reagents for the purposes of this invention are substances that enable the state of a chemical system to be characterized. The indicator includes a variety of acid/base indicators, metal indicators, redox indicators, dyes, absorption indicators and the like. Combinations of indicators may be used.

The choice of indicator depends on the type of fluid being tested and/or the parameters being determined such as the concentration of acidic or basic components, presence or concentration of metals, oxidative/reductive potential, identity markers or the presence of specific components to name a few. Further, "lock and key" type indicators are also included wherein a "lock", a material soluble in the fluid and stable to the conditions of use, is added to the fluid and an indicator, or "key", is chosen to specifically detect the lock. This concept may also take the form where a determined functional additive, present in the fluid for performance reasons, is targeted and a "key" is selected to indicate the presence of the "lock".

The indicators function by a variety of mechanisms both in how the specific parameter is determined in how the indicator responds. Examples of indicator responses include color changes as seen through visual colorimetry, photometry, fluorescence, chemiluminescence and the like. Combinations of indicator responses may be used.

The color of the indicator is chosen depending on the type of fluid being tested and/or the level of degradation of the fluid. Certain colors contrast strongly to the usual color of the fluid which is preferred. The choice of a suitable color may be determined by a particular application. For example, automatic transmission fluid for passenger cars is colored red for identification purposes. It would be inappropriate to use an indicator that turns red to indicate an unacceptable condition in the fluid.

Acid/base (pH) indicators include Malachite Green, Brilliant Green, Methyl Green, Picric acid, Cresol Red, Crystal Violet, Metanil Yellow, m-Cresol Purple, Thymol Blue, p-Xylenol Blue, Thymol Blue sodium salt, Quinaldine Red, Tropaeolin OO, 2,6-dinitrophenol, Phloxine B, 2,4-dinitrophenol, 4-dimethylaminoazobenzene, Bromochlorophenol Blue, Bromophenol Blue, bromophenol blue sodium salt, Congo Red, Methyl Orange, 2,5-dinitrophenol, 1-Naphthyl Red, bromocresol green, bromocresol green sodium salt, alizarin S, methyl red, methyl red sodium salt, bromophenol red, chlorophenol red, hematoxylin, litmus, bromocresol purple, 4-nitrophenol, bromoxylenol blue, alizarin, bromothymol blue, bromothymol blue sodium salt, nitrazine yellow, phenol red, phenol red sodium salt, cresol red, 3-nitrophenol, neutral red, 1-naphtholphthalein, ocresolphthalein, phenolphthalein, thymolphthalein, alizarin yellow GG, alkali blue, epsilon blue, indigo carmine, nile blue A and acid fuchsin and the like. Combinations may be used.

Absorption indicators include Fluorescein, Eosin, Phloxine, Rose Bengal and Rhodamine 6G and the like. Combinations may be used.

Metal indicators include Alizarin Complexone, Alizarin S, Arsenazo III, Aurintricarboxylic acid, 2,2'-Bipyidine, Bromopyrogallol Red, Calcon (Eriochrom Blue Black R), Calconcarboxylic acid, Chrome Azurol S, Chromotropic acid, disodium salt, Cuprizone, 5-(4-Dimethylamino-benzylidene) rhodanine, Dimethylglyoxime, 1,5-Diphenylcarbazide, Dithizone, Eriochrome Black T, Eriochrome Blue SE, Eriochrome Blue Black B, Eriochrome Cyanine R, Fluorescein Complexone, Glyoxalibis(2-hydroxylanil), Hematoxylin, 8-Hydroxyquinoline, 2-Mercaptobenzothiazole, Methylthymol Blue, Murexide, 1-Nitroso-2-naphthol, 2-Nitroso-1-naphthol, Nitroso-R-salt, 1,10-Phenanthroline, Phenylfluorone, Phthalein Purple, 1-(2-Pyridylazo)-naphthol, 4-(2-Pyridylazo)resorcinol, Pyrogallol Red, Sulfonazo III, 5-Sulfosalicylic acid, 4-(2-Thiazolylazo)resorcinol, Thorin, Thymolthalexon, Tiron, Tolurnr-3,4-dithiol, Xylenol Orange, Zincon and the like. Combinations may be used.

Redox indicators include Neutral Red, Safranine T or O, Indigo Carmine, Methylene Blue, Thionin, Thymolindophenol, 2,6-Dichlorophenolindophenol, Gallocyanine, Nile Blue, Variamine Blue, Diphenyl amine, Diphenylamine-4-sulfonic acid, barium salt, Tris(2,2dipyridyl)iron(II) sulfate, N-phenylanthranilic acid, Ferroin, Nitroferroin, 5,6-Dimethylferroin, 4-Amino-4'-methyldiphenylamine, Diphenylbenzindine-disulfonic acid, o-Dianisidine, 3,3'-Dimethylnaphthidine, 3,3'-Dimethylnaphthidine disulfonic acid and the like. Combinations may be used.

Marker substances include diazo dyes, anthraquinone dyes and the like, metals, metal salts, metal oxides, metal coordination complexes and the like or other substances compatible with the lubricant. It may be beneficial for the marker substance to be stable to the service conditions of the fluid, but it is not necessary. In general marker substances are used to identify new fluids. In some cases however, it could be useful to validate the identity of a fluid for, as an example, warranty claims. In this case the marker would need to survive and be detectable after experiencing the typical operating conditions of the fluid. Combinations of these substances may be used.

Developing agents are substances that will make conspicuous the presence or absence of a marker substance. Developing agents could include mineral or organic acids and the like, basic substances, oxidizing agents, reducing agents, chelating agents and the like. Combinations of developing agents may be used.

In one embodiment the preferred indicator is Alizarin for lubricating oils.

In one embodiment the present invention may use combinations of indicator reagents, combinations of developing agents and mixtures thereof.

Visual Indicia

Analysis in particular qualitative analysis of the reacted test sample is accomplished by visual inspection of the reacted test sample using the (provided) visual indicia as a guide. Analysis occurs after an effective period of time to allow for the reaction between the components of the fluid and the indicator. Generally the time for reaction is in the range of about 1 sec. to about 30 mins, in another embodiment about 1 minute to about 15 minutes and in another embodiment about 1 minute to about 5 minutes. The visual indicia include an artistic rendering, a reproduction of a photograph of a functional fluid in various conditions, color key, and the like. Combinations of visual indicia may be used. The visual indicia generally include one representation, two representations and more than two representations of the functional fluid disposed upon the test media. In one embodiment the preferred visual indicia is one in an unacceptable condition and one in acceptable condition or a marked and unmarked fluid or the like.

In one embodiment, it is preferred for the visual indicia as shown in FIG. 2. In FIG. 2 the engine oil has the characteristics of the engine oil in excellent condition; an oil in good condition, acceptable within the normal range for typical engine oil; and an engine oil at the limit of useful life requiring an oil change. A descriptive text corresponding to each of these examples may be provided in the kit.

In one embodiment is preferable that the visual indicia depicted be dispersed upon the same or similar medium provided in the kit, to assure that the kit user compares the sample to be tested to examples produced under similar conditions. It is to be understood that a different number of indicia than shown in FIG. 2 may be provided.

Solvents

The test medium can be dry or wet. In one embodiment where the test medium is wet it is due to the use of a solvent on the test medium. Suitable solvents include aliphatic, unsaturated and aromatic hydrocarbons, alcohols, glycols, glycol ethers, lower alcohols, such as methanol, ethanol and propanol, ethers, esters, amides, water and the like. Combination of solvents may be used. The solvent is used in the range of about 1% to about 99.9%, in one embodiment about 5% to about 98% and in another embodiment about 1% to about 95.5% of the indicator solution. The solvent used depends on the type of fluid being tested. Combinations of solvents are also useful when the indicator or developing agent, depending on the application and type of analysis desired, is not soluble in the fluid. Particularly, solvents or combinations of solvents which present a desirable combination of properties including good solvency power and miscibility with the fluid and the indicator or marker or development agent, low vapor pressure at ambient temperatures, high flash points and the like.

Method

The method comprises the steps of (a) obtaining a sample of a functional fluid, (b) placing the sample upon the test medium, (c) waiting for an effective period of time to allow for the reaction between the components of the fluid and the indicator or developer, d) making a visual determination of the test medium using the printed instructions and/or comparative visual indicia depicting the functional fluid in various conditions as a guide for qualitative determination.

It is not necessary that the sample be taken during actual operation of the engine or other equipment in order to obtain a representative sample of the functional fluid. The sample of functional fluid may be taken at any time before, during or after operation of the engine or equipment. The functional fluid sample can be new, used or combinations thereof.

The apparatus is comprised of a package that can be sealed containing the chemically treated test medium in either a wet or dry state and includes written instructions and a set of visual indicia depicting samples of the fluid disposed upon a test medium printed in color on the package with descriptive text. In one embodiment, the visual indicia should show a depiction of the fluid which is in an acceptable condition and one of the fluid in an unacceptable condition or with and without a marker substance.

For the analysis of the condition of a functional fluid, for instance as engine oil, under this invention is essentially dependent upon the reaction of components in the oil with an appropriate indicator. Engine oil, as it is used, becomes contaminated with acidic byproducts from oxidation, acidic components from fuel combustion and a component of sludge. The chemically basic additives, including detergents, which are added to the oil to neutralize these acidic components, are consumed over time. During the service life of the lubricant a point is reached where these basic components fall below a minimum acceptable level rendering the oil unacceptable for further use. Continued use of an unacceptable oil will likely cause damage to the engine. When a sample of used oil is obtained and the sample is placed upon a suitably treated test medium, the basic additives in the oil, if they have not been consumed, will react with the indicator changing its color. The presence or absence of a color change and the relative intensity of the color provides a means for qualitative analysis of the test sample.

In one embodiment the functional fluid is an engine oil. The engine oil sample under ordinary circumstances may be obtained using a dipstick provided as a part of the engine, transmission or other equipment under lubrication. The user will withdraw an amount of oil along with the dipstick and the dipstick may then be wiped on the test medium or the oil which will collect into a drop at the end of the dip stick may then placed upon the test medium. Typically, less that 1 milliliter of oil is necessary for the analysis. Once the oil test sample has been placed on the test medium, it will begin to react. The user allows for an effective period of time to allow for the reaction between the components of the fluid and the indicator. Next, the user determines whether or not a color change occurred, and refers to the visual indicia as a guide. The user may consult the descriptive text accompanying the example selected to determine the condition of the functional fluid.

SPECIFIC EMBODIMENT

Example 1

This example tests the quality of passenger car engine oil and consists of a test medium of Whatman filter paper, which has been soaked with a solution of ethanol or isopropanol (90% w/w), lauryl alcohol (10% w/w) and pH indicator (0.1% w/w). The pH indicator used is Alizarin (1,2-dihydroxyanthraquinone).

A used oil sample is placed on the wet filter paper and the basic additives (quantified as the TBN or Total Base Number, typically measured by ASTM D4739) of the oil react with the pH indicator inducing a color change from yellow to purple, with the indicator listed above, to a degree depending on the level of TBN. The intensity of the color change is reduced as the TBN drops over the service life of the oil until no purple color is apparent indicating the fluid has reached its maximum life. (See Table 1)

TABLE 1

Effect of TBN on Color Change

| Age of Sample | Total Base Number (ASTM D4739) | Appearance of the Paper | |
|---|---|---|---|
| | | After 1 Minute | After 5 Minutes |
| New | 5.6 mg KOH/g | Purple | Strong Purple |
| 2000 Miles | 4.1 | Faint purple | Purple |
| 6000 Miles | 1.9 | Brown spot, no purple apparent | Brown spot, no purple apparent |

The results in Table 1 demonstrate that an oil can be analyzed by visual indicia depicting the quality of the oil, as the brown color with no purple at 6000 miles indicates the condition of the oil.

While the invention has been illustrated and described, it will be appreciated that various changes can be made therein without departing from the spirit and scope of the invention, with the scope of the present invention being defined by the following claims.

We claim:

1. A method to analyze the condition of a functional fluid comprising:
   (1) obtaining a sample of the functional fluid,
   (2) placing the sample of the functional fluid on a test medium wherein the test medium comprises polymeric fibers,
   (3) reacting the functional fluid with an indicator in the test medium, and
   (4) analyzing visually the results of the reaction,
   resulting in the determination of the condition of the functional fluid; wherein the functional fluid is selected from the group consisting of transmission fluids, hydraulic fluids, transformer fluids, diesel, biofuels, and mixtures thereof;

wherein the test medium has a property selected from the group consisting of a porosity, a density, a wicking ability and combinations thereof to provide rapid dispersion on the functional fluid; and;

wherein the indicator is selected from the group consisting of Neutral Red, Safranine T or O, Indigo Carmine, Methylene Blue, Thionin, Thymolindophenol, 2,6-Dichlorophenolindophenol, Gallocyanine, Nile Blue, Variamine Blue, Diphenyl amine, Diphenylamine-4-sulfonic acid, barium salt, Tris(2,2dipyridyl)iron (II) sulfate, N-phenylanthranilic acid, Ferroin, Nitroferroin, 5,6-Dimethylferroin, 4-Amino-4'-methyldiphenylamine, Diphenylbenzindinedisulfonic acid, o-Dianisidine, 3,3'-Dimethylnaphthidine, 3,3'-Dimethylnaphthidine disulfonic acid and combinations thereof.

2. The method of claim 1 comprising the steps of determining the condition of the functional fluid selected from the group consisting of visually comparing the test medium against a set of comparative visual indicia depicting the functional fluid in at least two different conditions as a guide; using the printed instructions as a guide; and combinations thereof.

3. The method of in claim 1, wherein the test medium comprise paper, cellulosic material polymeric fiber, polypropylene woven fabric, nonwoven fabric, metal, glass, plastic, composite material or combinations thereof.

4. The method of claim 3 wherein the test medium comprises paper, cellulosic material, cellulose nitrate, cellulose acetate wood, chromatography paper, filter paper, polymeric fibers, natural fibers, finely woven fabrics, metal, glass, glass micro fiber, sintered glass, silica coated surfaces, alumina coated surfaces, thin layer chromatography plates, plastic, plastic laminated material, composites or combinations thereof.

5. The method of claim 1 wherein step (3) further comprises the use of one or more acid indicators, base indicators, pH indicators, metal indicators, organic indicators, inorganic salts indicators, absorption indicators, dyes and combinations thereof.

6. The method of claim 5 wherein the acid/base indicator is selected from the group consisting of malachite green, brilliant green, methyl green, picric acid, cresol red, crystal violet, metanil yellow, cresol red, crystal violet, metanil yellow, mpcresol purple, thymol blue, p-Xylenol blue, thymol blue sodium salt, quinaldine red, tropaeolin OO, 2,6-dinitrophenol, dimethylaminoazobenzene, bromochlorophenol blue, bromophenol blue, bromophenol blue sodium salt, congo red, methyl orange, 2,5-dinitrophenol, 1-naphthyl, bromocresol green, bromocresol green sodium salt, alizarin S, methyl red, methyl red sodium salt, bromophenol red, chlorophenol red, hematoxylin litmus, bromocresol purple, nitrophenol, bromoxylenol blue, alizarin, bromothymol blue, bromothymol blue sodium salt, nitrazine yellow, phenol red, phenol red sodium salt, cresol red, 3-nitrophenol, neutral red, 1-naphtholphthalein, o-cresolphthalein, phenolphthalein, thymolphthalein, alizarin yellow, alkali blue, epsilon blue, indogo carmine, nile blue, acid fuchsin, fluorescein, eosin, phloxine, rose bengal, rhodamine and combinations thereof.

7. The method of claim 5 wherein the metal indicator is selected from the group consisting of Alizarin Complexone, Alizarin S, Arsenazo III, Aurintricarboxylic acid, 2,2'-Bipyidine, Bromopyrogallol Red, Calcon (Eriochrom Blue Black R), Calconcarboxylic acid, Chrome Azurol S,Chromotropic acid, disodium salt, Cuprizone, 5-(4-Dimethylamino-benzylidene)rhodanine, Dimethylglyoxime,1,5-Diphenylcarbazide, Dithizone, Eriochrome Black T, Eriochrome Blue SE, Eriochrome Blue Black B, Eriochrome Cyanine R, Fluorescein Complexone, Glyoxalibis(2-hydroxyanil), Hematoxylin, 8-Hydroxyquinoline, 2-Mercaptobenzothiazole, Methylthymol Blue, Murexide, 1-Nitroso-2-naphthol, 2-Nitroso-1-naphthol, Nitroso-R-salt, 1,10-Phenanthroline, Phenylfluorone, Phthalein Purple, 1-(2-Pyridylazo)-naphthol, 4-(2-Pyridylazo)resorcinol, Pyrogallol Red, Sulfonazo III, 5-Sulfosalicylic acid, 4-(2-Thiazolylazo)resorcinol, Thorin, Thymolthalexon, Tiron, Tolurnr-3,4-dithiol, Xylenol Orange, Zincon and combinations thereof.

8. The method of claim 1 comprising a marker substance in the test medium that is compatible with the lubricant and wherein the marker is selected from the group consisting of metals, metal salts, metal oxides, metal coordination complexes, other substances and combinations thereof.

9. The method of claim 1 comprising a developing agent is selected from the group consisting of mineral or organic acids and the like, basic substances, oxidizing agents, reducing agents, chelating agents and combinations thereof.

10. The method of claim 9 wherein the test medium is treated with a developer or detector reagent for the purposes of reacting with a marker substance to cause a color change, chemiluminescence, phosphorescence, fluorescence or combinations thereof.

11. The method of claim 1 wherein the test medium has a solvent.

12. The method of claim 11 wherein the solvent is selected from the group consisting of aliphatic and aromatic hydrocarbons, alcohols, glycols, glycol ethers, lower alcohols, such as methanol, ethanol and propanol, ethers, esters, water and combinations thereof.

13. A method to analyze the condition of a functional fluid comprising:
(1) obtaining a sample of the functional fluid,
(2) placing the sample of the functional fluid on a test medium wherein the test medium comprises polymeric fibers,
(3) reacting the functional fluid with an indicator in the test medium, and
(4) analyzing visually the results of the reaction,
resulting in the determination of the condition of the functional fluid; wherein the functional fluid is selected from the group consisting of engine oils, transmission fluids, greases, gear oils, hydraulic fluids, transformer fluids, diesel, biofuels, and mixtures thereof;
wherein the indicator is selected from the group consisting of Neutral Red, Safranine T or O, Indigo Carmine, Thionin, Thymolindophenol, 2,6-Dichlorophenolindophenol, Gallocyanine, Nile Blue, Variamine Blue, Diphenyl amine, Diphenylamine-4-sulfonic acid, barium salt, Tris (2,2dipyridyl)iron(II) sulfate, N-phenylanthranilic acid, Ferroin, Nitroferroin, 5,6-Dimethylferroin, 4-Amino-4'-methyldiphenylamine, Diphenylbenzindinedisulfonic acid, o-Dianisidine, 3,3'-Dimethylnaphthidine, 3,3'-Dimethylnaphthidine disulfonic acid, alizarin and combinations thereof.

* * * * *